United States Patent [19]

Cartmell et al.

[11] Patent Number: 5,501,661
[45] Date of Patent: Mar. 26, 1996

[54] METHOD OF MAKING A WOUND DRESSING PRODUCT CONTAINING A POROUS LAYER

[75] Inventors: James V. Cartmell, Xenia; Wayne R. Sturtevant, Centerville; William E. Bausmith, III, Batavia; Michael L. Wolf, West Milton, all of Ohio

[73] Assignee: New Dimensions in Medicine, Inc., Dayton, Ohio

[21] Appl. No.: 435,307

[22] Filed: May 5, 1995

Related U.S. Application Data

[62] Division of Ser. No. 372,851, Jan. 13, 1995, which is a continuation of Ser. No. 130,698, Oct. 4, 1993, abandoned, which is a continuation-in-part of Ser. No. 68,633, May 27, 1993, Pat. No. 5,423,737.

[51] Int. Cl.⁶ .................................................. A61F 13/00
[52] U.S. Cl. .................... 602/58; 602/42; 602/48; 602/57; 424/443; 424/445; 424/447; 604/304
[58] Field of Search .................... 602/41–45, 48, 602/54, 57, 58; 424/443, 445, 446, 447; 604/20, 368, 378, 307, 304

[56] References Cited

U.S. PATENT DOCUMENTS

| | | |
|---|---|---|
| 3,072,249 | 1/1963 | Tritsch . |
| 3,998,215 | 12/1976 | Anderson et al. . |
| 4,646,731 | 3/1987 | Brower . |
| 4,744,355 | 5/1988 | Faase, Jr. . |
| 4,753,232 | 6/1988 | Ward . |
| 4,884,563 | 12/1989 | Sessions . |
| 4,909,244 | 3/1990 | Quarfoot et al. . |
| 5,000,172 | 3/1991 | Ward . |
| 5,060,642 | 10/1991 | Gilman . |
| 5,106,629 | 4/1992 | Cartmell et al. . |
| 5,115,801 | 3/1992 | Cartmell et al. . |
| 5,160,328 | 11/1992 | Cartmell et al. . |
| 5,204,110 | 4/1993 | Cartmell et al. ................. 424/443 |
| 5,423,736 | 6/1995 | Cartmell et al. ................. 602/42 |
| 5,423,737 | 6/1995 | Cartmell et al. ................. 602/57 |

FOREIGN PATENT DOCUMENTS

| | | |
|---|---|---|
| 106440 | 4/1984 | European Pat. Off. . |
| 168174 | 6/1985 | European Pat. Off. . |
| 413251 | 2/1991 | European Pat. Off. . |
| 2128479 | 10/1983 | United Kingdom . |
| PCT/US89/ 03913 | 4/1990 | WIPO . |

Primary Examiner—Richard J. Apley
Assistant Examiner—Kim M. Lee
Attorney, Agent, or Firm—Killworth, Gottman Hagan & Schaeff

[57] ABSTRACT

A flexible wound dressing product contains a clear hydrogel material in a gel-like phase. The wound dressing product is comprised of several layers including a wound dressing, optional removable tab and optional release liner. The wound dressing comprises a thin-film layer, an adhesive layer, porous backing layer, optional support layer and a hydrogel material. The thin-film layer has a center portion and a perimeter portion. The backing layer, support layer and hydrogel material, which together form a reinforced hydrogel patch, are positioned in the center portion of the thin-film layer. The porous backing layer is formed of a porous material having sufficient porosity that the backing layer can be secured to the hydrogel material without the use of an adhesive. During manufacture, the hydrogel patch is assembled in sheet form and subsequently cut to a desired size and shape.

8 Claims, 5 Drawing Sheets

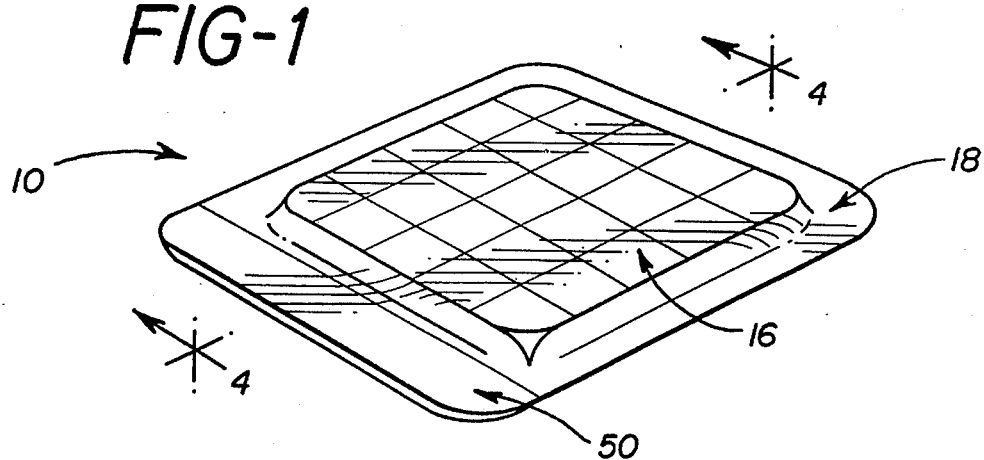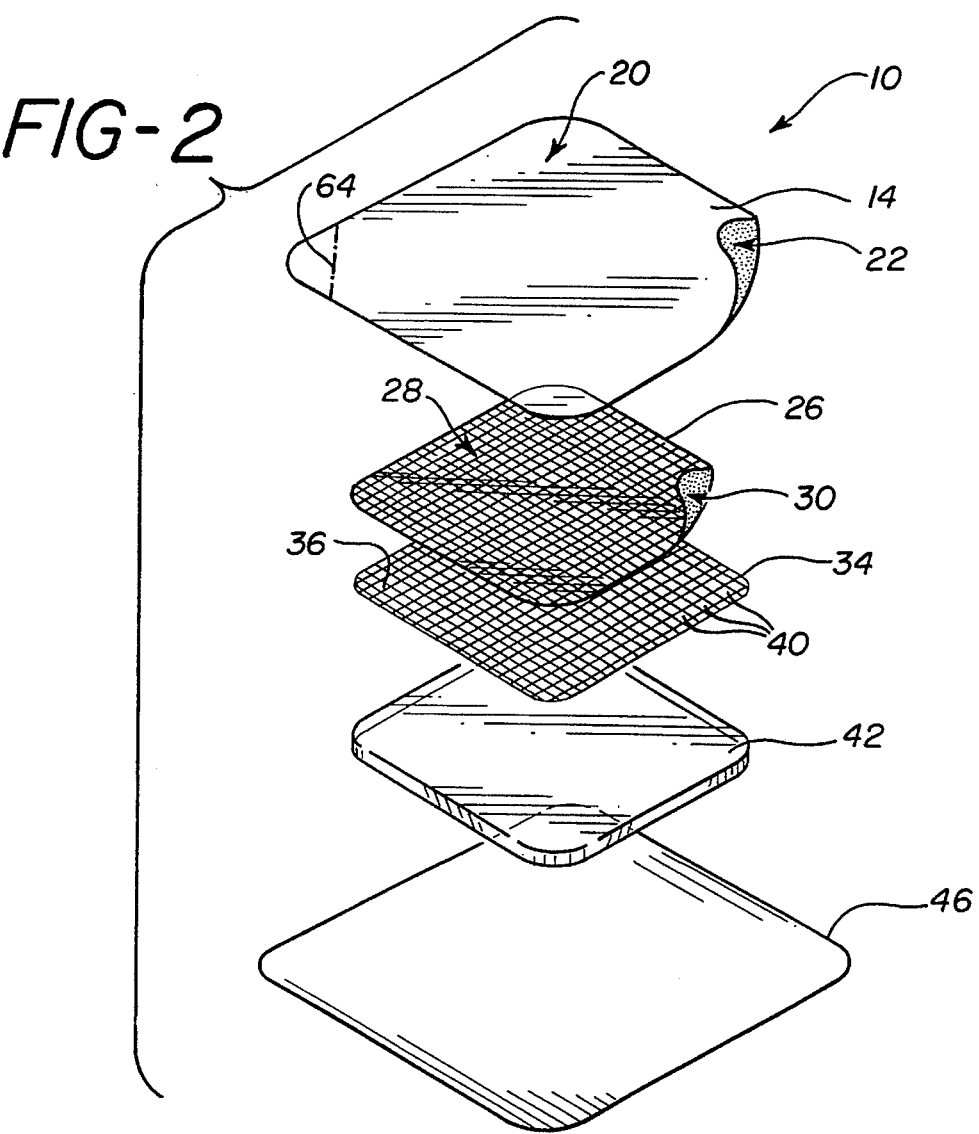

METHOD OF MAKING A WOUND DRESSING PRODUCT CONTAINING A POROUS LAYER

This application is a division of U.S. application Ser. No. 08/372,851 filed Jan. 13, 1995, which is a continuation of application Ser. No. 08/130,698 filed Oct. 4, 1993 and now abandoned which is a continuation-in-part of Ser. No. 08/068,633 filed May 27, 1993 and now U.S. Pat. No. 5,423,737.

BACKGROUND OF THE INVENTION

The present invention relates to wound dressings and, more particularly, to a flexible wound dressing product containing a hydrogel substance and a porous layer.

Secreting skin wounds, such as decubitus ulcers and open surgical wounds, have long presented a medical challenge in keeping such wounds sterile and relatively dry. The accumulation in wound crevices of wound exudate, such as blood, pustulation and other wound fluids, promotes growth of bacteria and crusted organisms which cause infection and delay the healing process. However, since it is often desirable to allow a wound to heal in a slightly moist or occlusive state, as it is believed that this may accelerate healing, excess wound exudate must be removed. If excess wound exudate remains on a wound, a "blister" of exudate can form under the wound dressing which is not only unsightly, but also may cause the dressing to leak, thereby defeating the aim of sterility. Existing methods of aspiration, however, can lead to wound infection or can destroy sterility. Additionally, it is not desirable to remove all exudate, as that would result in a dry wound and, hence, a slower healing process.

Known aqueous moisture-absorbing wound dressing systems have additional problems in that the aqueous material is generally contained in the center portion of a wound dressing, with a bulky adhesive border, such as a foam border. Problems with such borders include decreased comfort, conformity and adhesion, as well as the existence of a "lifting edge" that can catch on clothes or bed sheets, thereby exposing the wound to bacteria and infection. In addition, observation of the wound by medical personnel may require lifting the wound dressing, thereby exposing the wound, again creating a situation where bacteria and infection can be introduced to the wound site.

Our own commonly-assigned U.S. Pat. No. 5,106,629, issued Apr. 21, 1992, to Cartmell et al., discloses a hydrogel wound dressing with a thin-film transparent layer, a dimensionally stable backing layer over the outer surface of the transparent layer, and a release liner. The backing layer and the release liner each have a corner tab to facilitate the peeling of each from the transparent layer. The hydrogel material is positioned in a center portion of the transparent layer, and the adhesive perimeter portion of the transparent layer adheres to the skin of the patient. The dimensionally stable backing member prevents the transparent layer from curling and facilitates handling of the dressing during its application.

Many prior art wound dressings contain layers constructed of polyurethane or other polymeric material. Such materials, however, have limited moisture/vapor permeability characteristics. The wound is often not able to breathe adequately. In addition, many wound dressings are difficult to handle and apply to the wound without touching the adhesive portion of the wound dressing.

It is seen, therefore, that there is a need for a hydrogel wound dressing product that is easily handled during application to the wound without touching the adhesive side of the dressing. Further, there is a need for a hydrogel wound dressing product that contains a porous, moisture- and vaporpermeable layer.

SUMMARY OF THE INVENTION

The present invention meets these needs by providing a thin-film wound dressing containing a hydrogel material. The present invention also provides a method of manufacture of the wound dressing product. The wound dressing product herein can be manufactured to any desirable size to provide a thin-film, fluid-absorbing dressing for a wound of any size. The wound dressing herein is conformable, adhesive around its perimeter portion, and nonadhesive over the wound site. The present invention also includes a moisture- and vapor-permeable porous layer which permits the transpiration of moisture through the wound dressing.

The wound dressing product of the present invention comprises an optional release liner, an optional removable tab, and wound dressing. The wound dressing comprises a thin-film layer, preferably composed of polyurethane, an adhesive layer, a porous backing layer, an optional support layer and a hydrogel material. The thin-film layer, which may be of any suitable shape, but which typically is generally rectangular in shape, may have a center portion and a perimeter portion surrounding the center portion, in addition to a first side and an opposing second side. When the dressing is applied to the wound, the first side of the thin-film layer forms the outer surface of the dressing product. The thin-film layer may, alternatively, be constructed of materials other than polyurethane, such as polyethylene, vinyl, or other suitable materials, and may also be perforated throughout in order to improve the moisture- and vapor-permeability of the wound dressing.

The adhesive layer is positioned on the second side of the thin-film layer. The backing layer is constructed of a porous material comprising a filled polyolefin foam, wherein the porous material has a porosity ranging from about 30% to about 80%. The porous backing layer has a first side and an opposing second side, and is adhered to the second side of the thin-film layer by means of the adhesive layer. The optional support layer is made from a material such as woven and nonwoven fabrics, gauze, scrim or other similar materials. The hydrogel material may be secured to the second side of the support layer. The permeable fabric of the support layer allows the hydrogel material to pass through to the first side of the support layer, resulting in the presence of the hydrogel layer on the first, as well as the second, side of the support layer. As such, the first side of the support layer, along with the hydrogel layer, is secured to the second side of the porous backing layer. The backing layer possesses sufficient porosity to allow an adhesive contact to be made between the backing layer and the hydrogel material present on the first side of the support layer. The porous backing layer obviates the need for a second adhesive layer, and is moisture- and vapor-permeable.

The optional support layer adds increased stability and support to the hydrogel material. In embodiments in which the support layer is not used, the hydrogel material is secured directly to the second side of the porous backing layer.

The hydrogel material is preferably a saline solution in an aqueous gel-like phase, and is contained within the center portion of the thin-film layer. The gel-like consistency of the hydrogel material creates a bond between the wound dressing and the wound site without creating an actual adhesive attachment that would damage new cell tissue upon removal. An advantage of the gel-like hydrogel is that it will not deteriorate as the wound fluids are absorbed. Additionally, it permits clean and neat removal of the wound dressing when the wound heals or the dressing is changed.

The optional release liner, which is preferably silicone-coated, overlies the hydrogel material and is secured to the perimeter portion of the second side of the thin-film layer by means of the adhesive layer. The optional removable tab is interposed between the thin-film layer and the release liner. The tab is adhered to one edge of the perimeter portion of the second side of the thin-film layer by means of the adhesive layer so as to provide a free grippable surface to allow for the removal of the release liner from the thin-film layer and to facilitate the handling of the wound dressing during application of the dressing to the wound. In one embodiment, the porous backing layer and/or the thin-film layer may be flesh-colored, in order to make the wound dressing product less conspicuous on the patient's skin.

In accordance with one aspect of the present invention, the optional removable tab is flat and is constructed of double-coated paper, polystyrene, polyester, or other suitable material. Alternatively, the tab may comprise a V-shaped member that is preferably silicone-coated. This V-shaped member has a first flap and a second flap, with the first flap being secured to the second side of the thin-film layer by means of the adhesive layer, and the second flap being positioned between the first flap and the release liner. The open end of the V-shaped member is positioned along one edge of the thin-film layer and the opposing edge of the release liner. In both embodiments, the tab is removable by peeling after the wound dressing is applied to the patient's skin. The tab also aids in adding stability to the thin-film layer as the release liner is removed from the thin-film layer.

The release tab may also be eliminated altogether. In its place, the adhesive layer is applied to the second side of the thin-film layer so as to leave an edge or corner of the thin-film layer uncoated with adhesive. The wound dressing may then be removed from the release liner, without the use of a separate removable tab, by grasping the uncoated edge or corner of the thin-film layer. The uncoated portion of the thin-film layer may also be perforated or otherwise detachable by tearing.

The present invention also provides a method of manufacturing the wound dressing product. Initially, the thin film is provided, preferably of a polyurethane material. This film contains center and perimeter portions, along with a first side and an opposing second side. The second side of the thin film is coated with a preferably medical-grade adhesive layer. A porous backing layer having a first side and second side is then provided. A support layer having a first side and a second side may also be provided. The support layer comprises a material such as woven and nonwoven fabrics, gauze, scrim or other similar materials. A hydrogel material is then applied to the second side of the support layer. The interstices within the fabric of the support layer allow the hydrogel material to flow through to the first side of the support layer, such that the hydrogel layer resides on both the first and second sides of the support layer. As such, the first side of the support layer, along with the hydrogel layer, is secured to the second side of the porous backing layer. The backing layer possesses sufficient porosity to allow an adhesive-like contact to be made between the backing layer and the hydrogel material present on the first side of the support layer. The porous backing layer obviates the need for a second adhesive layer, and is moisture- and vapor-permeable. Together, the backing layer, support layer and hydrogel material form a reinforced hydrogel patch.

Preferably, the hydrogel patch is manufactured in sheet form and cut to various sizes. The size of the thin-film layer is selected accordingly in order that the center portion of the thin-film layer is capable of accommodating the hydrogel patch. The hydrogel patch is then secured to the thin-film layer such that the first side of the backing layer adheres to the center portion of the second side of the thin-film layer by means of the adhesive layer.

A release liner, preferably of a silicone-coated sheet material, is provided. An optional removable tab having first and second sides may also provided. The first side of the tab is laminated to one edge of the perimeter portion on the second side of the thin-film layer, such that the adhesive layer is positioned between the tab and the thin-film layer. A first side of the release liner is then laminated to the perimeter portion on the second side of the thin-film layer by means of the adhesive layer. When the wound dressing product is fully assembled, the release liner overlies the hydrogel material and patch. In fact, the release liner, thin-film layer and adhesive layer may be constructed to form an adhesive seal around the hydrogel material, thus preserving sterility of the wound dressing.

In accordance with one aspect of the present invention, a flat tab constructed of a double-coated paper may be provided. Alternatively, a flat tab constructed of polystyrene, polyester, or other suitable material may be used. In a second embodiment, a tab comprising a V-shaped member may be provided and is preferably silicone-coated. The V-shaped member has a first flap and a second flap, and the first flap is secured to the perimeter portion of the second side of the thin-film layer by the adhesive layer, while the second flap is positioned between the first flap and the release liner with the open end of the "V" positioned along one edge of the thin-film layer and the opposing edge of the release liner. In both embodiments, this tab may be removed by peeling after the dressing is applied to the patient's skin.

In accordance with another aspect of the present invention, the removable tab is eliminated. Instead, the adhesive layer is applied to the thin-film layer in such a manner as to leave an uncoated edge or corner. This uncoated edge or corner provides a grippable surface to allow for removal of the wound dressing from the release liner without the use of a separate tab.

In accordance with yet another aspect of the present invention, the support layer is eliminated. The hydrogel material is applied directly to the second side of the porous backing layer. The backing layer possesses sufficient porosity to allow the hydrogel material to adhere to the backing layer without the use of a separate adhesive layer between the backing layer and hydrogel material.

It is an object of the present invention to provide a wound dressing product containing a hydrogel substance which is particularly advantageous when used to dress exuding wounds, such as decubitus ulcers, by providing a skin-like media which is biocompatible, nonirritating, fluid-absorbing, and bacterial-protective; to provide a wound dressing that is easily handled and applied to a wound without touching the adhesive portion of the dressing; and to provide a wound dressing containing a highly porous backing layer which adheres to the hydrogel material without the use of an adhesive layer, thus providing a wound dressing that is less expensive to manufacture and has fewer materials than existing wound dressings.

Other objects and advantages of the invention will be apparent from the following description, the accompanying 10 drawings and the appended claims.

BRIEF DESCRIPTION OF THE DRAWINGS

FIG. 1 is a perspective view of the wound dressing product.

FIG. 2 is an exploded perspective view, illustrating the layers which form a preferred embodiment of the wound dressing product.

DETAILED DESCRIPTION OF THE PREFERRED EMBODIMENTS

The present invention relates to a wound dressing product for application to a wound which includes a wound dressing comprised of a thin-film layer and a hydrogel patch. The invention also includes a method of manufacture for the disclosed wound dressing product.

Referring to FIG. 1, the wound dressing product 10 of the present invention is shown. Although the wound dressing product 10 illustrated in FIG. 1 has a rectangular shape, it may be any of a variety of desired shapes, including a more elongated rectangular shape. The wound dressing product 10 is composed of several layers, as illustrated by the exploded view of FIG. 2 and the exploded side view of FIG. 3.

Figure 3:
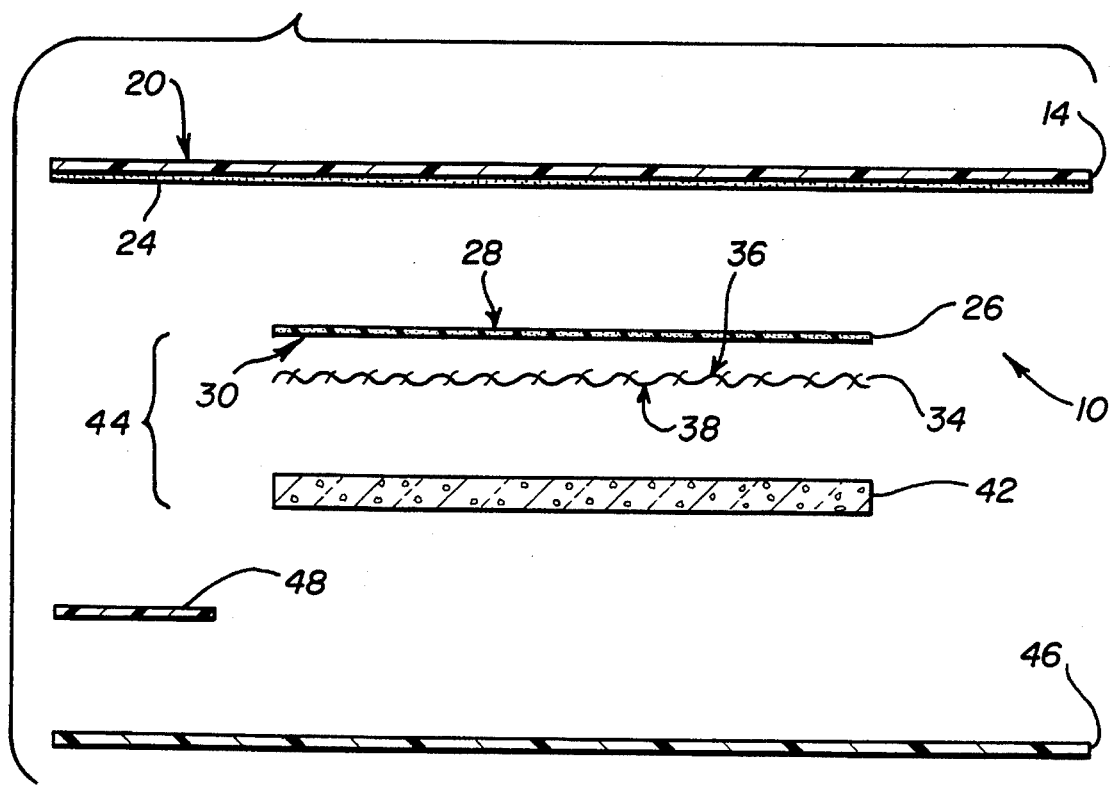
FIG. 3 is an exploded side view of the wound dressing product of FIG. 2, with the addition of the optional removable tab.

Referring, collectively, to FIGS. 1, 2 and 3, the wound dressing product 10 includes a thin-film layer 14, preferably of polyurethane, which may have a center portion 16 and a perimeter portion 18. The perimeter portion 18 may completely surround the center portion 16 of thin-film layer 14 or, alternatively, the center portion 16 may extend to the edges of two opposing sides of said thin-film layer 14. The thin-film layer 14 has a first side 20 and a second side 22, the second side 22 being coated with an adhesive layer 24. Backing layer 26, preferably constructed of a porous material comprising a foam material including silica and a polyolefin, and having a first side 28 and a second side 30, is adhered to the second side 22 of thin-film layer 14 by means of adhesive layer 24. The wound dressing further comprises an optional support layer 34 having a first side 36 and a second side 38, which is made from a material such as woven and nonwoven fabrics, gauze, scrim or other similar materials.

A hydrogel material 42 is adhered to the second side 38 of support layer 34. The permeable fabric of the support layer 34 contains interstices 40 which allow the hydrogel layer 42 to pass through to the first side 36 of support layer 34, resulting the presence of hydrogel layer 42 on both the second side 38 and the first side 36 of support layer 34. The hydrogel material 42 is preferably a saline solution in an aqueous gel-like phase. The first side 36 of support layer 34 is attached to the second side 30 of porous backing layer 26. The hydrogel material 42 residing on first side 36 of support layer 34 forms an adhesive-like bond between the support layer 34 and the second side 30 of backing layer 26.

Backing layer 26 is porous to the extent that it adheres to hydrogel material 42 without the use of a separate adhesive layer and, preferably, has a porosity ranging from about 30% to about 80%. As is well known in the art, porosity is defined as the percentage of the total volume occupied by minute channels or open spaces within the material. The preferred porous material is a microporous synthetic sheet commercially available from PPG Industries, Inc., under the trademark Teslin®. Those skilled in the art will understand that the extent to which the porous material must be porous will depend upon the particular gel material chosen to form the hydrogel material 42. Further, those skilled in the art will appreciate that sufficiently porous materials other than those described herein may be used without departing from the scope of the invention.

The hydrogel material 42, optional support layer 34 and backing layer 26 together form a hydrogel patch 44, which is contained within the center portion 16 of thin-film layer 14. In one embodiment of the present invention, the center portion 16 extends to the edges of two opposing sides of thin-film layer 14, and the hydrogel patch 44 is substantially aligned along two opposing sides with said thin-film layer 14. An optional release liner 46, preferably of a silicone-coated sheet material, may overlay the hydrogel material 42 and may be secured to the perimeter portion 18 of the second side 22 of thin-film layer 14 by means of adhesive layer 24. One skilled in the art will recognize that the release liner 46 may be eliminated and that the wound dressing may, instead, be stored in an air-tight package in order to preserve the sterility of the wound dressing 12 and the gel-like consistency of the hydrogel material 42.

Figure 4:
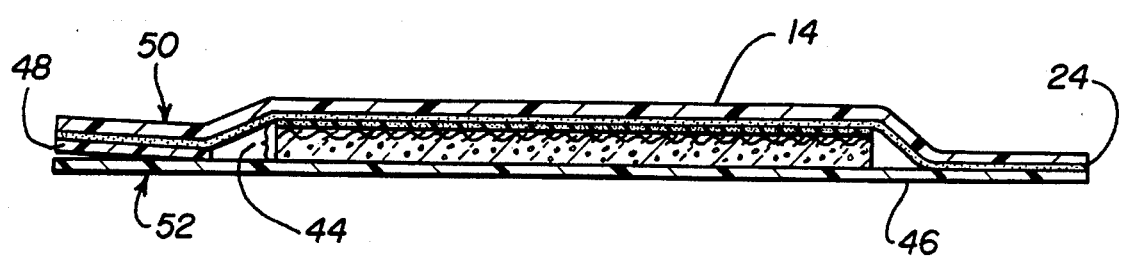
FIG. 4 is a cross-sectional view of the wound dressing product of FIG. 1 taken along line 4—4.
Figure 5:
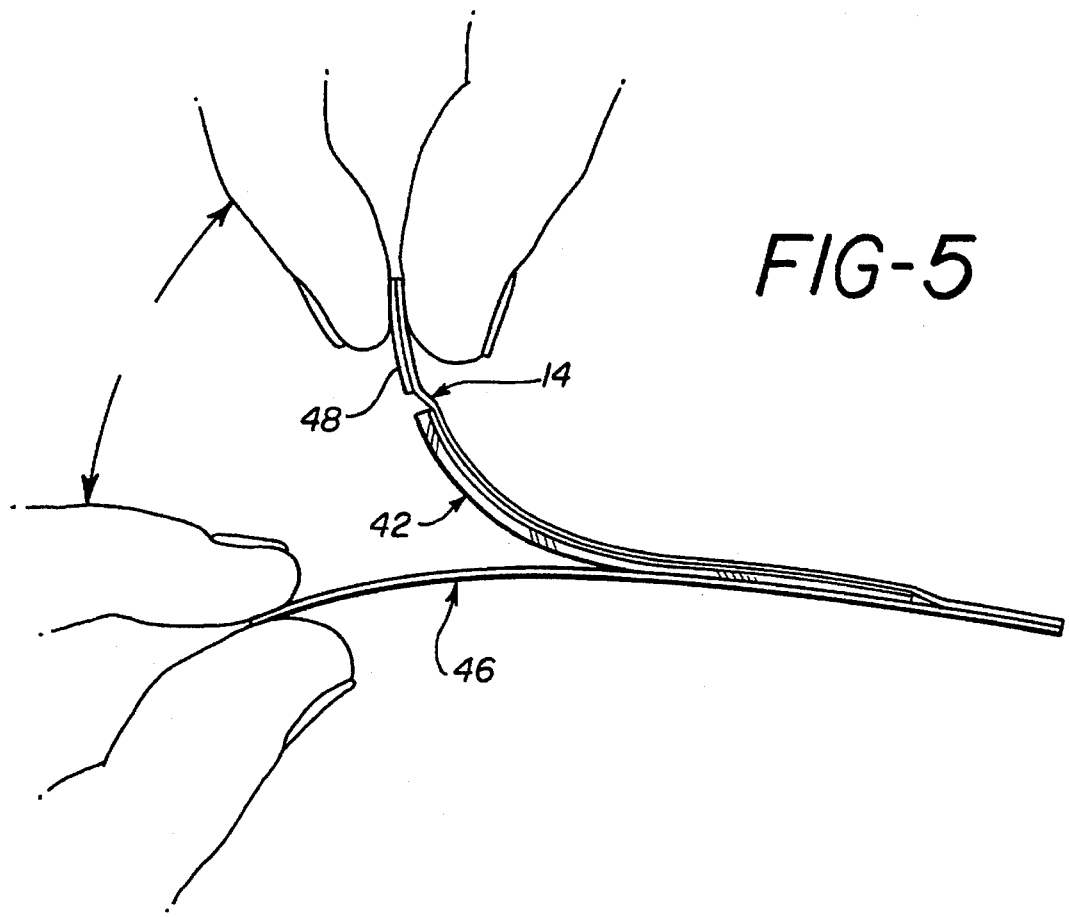
FIG. 5 is a side view of the wound dressing product which illustrates the peeling of the release liner from the wound dressing.
Figure 6:
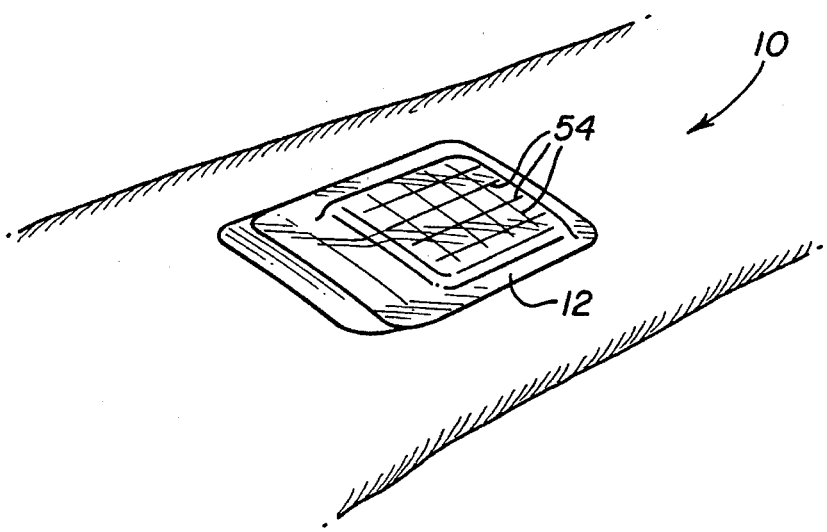
FIG. 6 is a perspective view showing the wound dressing in place on the patient's skin.

Referring now to FIGS. 4–6, collectively, an optional removable tab 48 may be interposed between the thin-film layer 14 and the release liner 46. The tab 48 is adhered to one edge 50 of the perimeter portion 18 of thin-film layer 14 by means of the adhesive layer 24, so as to provide a grippable surface to allow for the removal of the release liner 46 from thin-film layer 14 and to facilitate the handling of the wound dressing 12 during application of the wound dressing 12 to the wound.

The gel-like consistency of the hydrogel material 42 creates a bond between the wound dressing 12 and the wound site without creating an actual adhesive attachment that would damage new cell tissue upon removal. An advantage of the gel-like hydrogel material 42 is that it will not deteriorate as the wound fluids are absorbed. Additionally, it permits clean and neat removal of the wound dressing 12 when the wound heals or the dressing 12 is changed.

Figure 7:
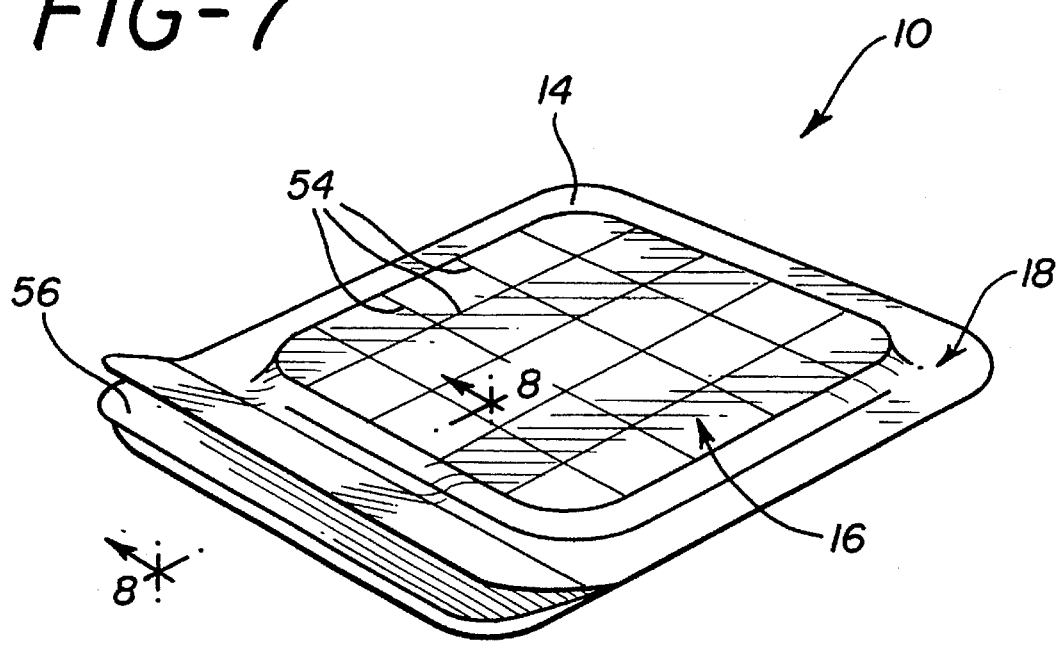
FIGS. 7 and 8 illustrate a second preferred embodiment in which the flat, polystyrene tab of FIGS. 1–6 is replaced with a V-shaped tab.
Figure 8:
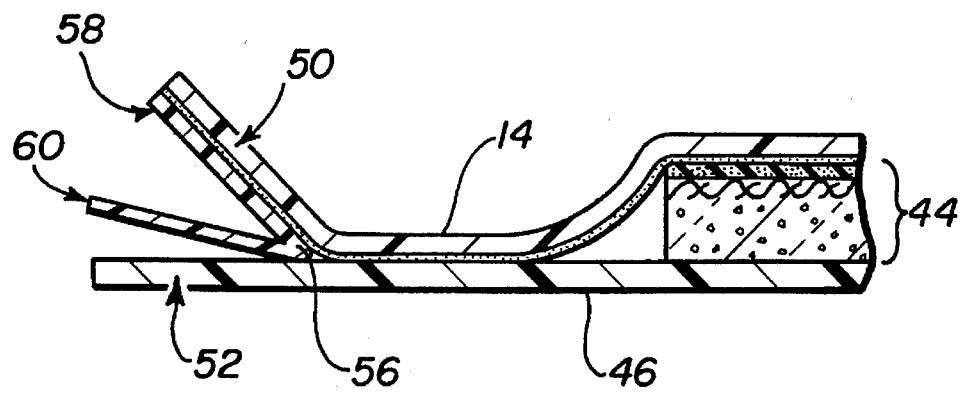

In one embodiment of the present invention, the optional removable tab 48 is constructed of a double-coated paper, polystyrene, polyester, or other suitable material, and is preferably flat, as shown in FIGS. 1 and 3–6. FIGS. 7 and 8 illustrate a second embodiment, wherein the flat tab 48 is replaced with a V-shaped member 56. The V-shaped member 56 has a first flap 58 and a second flap 60, with the first flap 58 being secured to one edge 50 of the second side 22 of thin-film layer 14 by means of adhesive layer 24, and the second flap 60 being positioned between first flap 58 and one edge 52 of release liner 46. The V-shaped member 56 and the release liner 46 are preferably coated with silicone. This enables the V-shaped member 56 to be more easily removed from the thin-film layer 14, and enables the release liner 46 to be more easily removed from the thin-film layer 14 and hydrogel material 42. Both the tab 48 and the V-shaped member 56 are removable by peeling after the wound dressing 12 is applied to the wound site. The tab 48 and V-shaped member 56 also aid in adding stability to the thin-film layer 14 as release liner 46 is removed from the wound dressing product 10.

Alternatively, tab 48 and V-shaped member 56 may be eliminated altogether. Adhesive layer 24 may be applied to thin-film layer 14 in such a manner as to leave a portion of thin-film layer 14 uncoated. As illustrated in FIG. 2, nonadhesive portion 64 provides a grippable surface to facilitate removal of thin-film layer 14 from release liner 46. One skilled in the art will appreciate that a number of possible locations exist on thin-film layer 14 for placement of nonadhesive portion 64; nonadhesive portion 64 need not be located on a corner of thin-film layer 14.

Figure 9A:
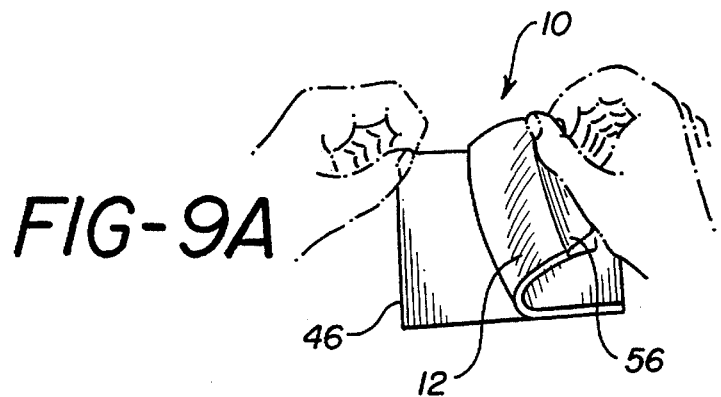
FIGS. 9A through 9D illustrate the preferred method of application of the wound dressing product of the present invention.
Figure 9B:
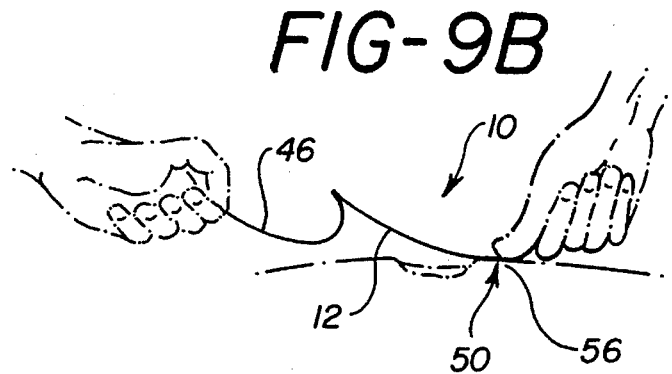
Figure 9C:
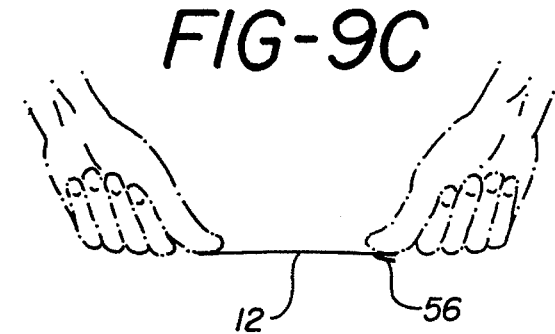
Figure 9D:
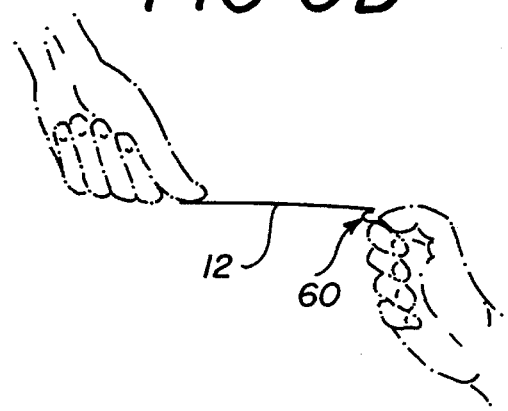

FIGS. 9A through 9D illustrate the preferred method of application of the wound dressing product 10 to a wound. Although these figures illustrate the application of a wound dressing 12 having a V-shaped member 56, a similar procedure may be used to apply the wound dressing 12 of FIGS. 2–5 wherein a flat tab 48 or nonadhesive portion 64 is utilized. As shown in FIG. 9A, the release liner 46 is first removed from the wound dressing 12 by grasping V-shaped member 56 and one edge 50 of thin-film layer 14 with one hand, while grasping release liner 46 with the other hand. After the edge 50 of thin-film layer 14 is removed from release liner 46, edge 50 is applied to the skin surrounding the wound of the patient. Edge 50 is then held in place while the release liner 46 is fully removed from wound dressing 12, as shown in FIG. 9B. After release liner 46 is removed, the wound dressing 12 is secured to the wound, as illustrated in FIG. 9C. As shown in FIG. 9D, V-shaped member 56 is then removed by pulling flap 60 with one hand while the opposite end of thin-film layer 14 of wound dressing 12 is held against the skin by the other hand. The present invention also provides a method of manufacturing the wound dressing product 10. Initially, a thin-film layer 14 is provided, preferably of a polyurethane material. Alternatively, thin-film layer 14 may be constructed of polyethylene, vinyl, or any other suitable material, and may be perforated throughout to allow air to contact the skin of the patient. This thin-film layer 14 contains a center portion 16 and a perimeter portion 18, along with a first side 20 and a second side 22. The second side 22 of the thin-film layer 14 is coated with a preferably medical-grade adhesive layer 24. A porous backing layer 26 having a first side 28 and a second side 30 is then provided. A support layer 34 having a first side 36 and a second side 38 is also provided. The support layer 34 comprises a material such as woven and nonwoven fabrics, gauze, scrim or other similar materials. A hydrogel material 42 is then applied to the second side 38 of the support layer 34. The support layer 34 is permeable and contains interstices 40 within the fabric which allow the hydrogel layer 42—which, when applied to support layer 34, is in liquid form—to flow through to the first side 36 of the support layer 34, such that the hydrogel layer 42 resides on both the first side 36 and the second side 38 of the support layer 34. The first side 36 of support layer 34 is laminated to the second side 30 of the backing layer 26.

The backing layer 26 preferably is formed of a porous material comprising a filled polyolefin foam, wherein the porous material has a porosity ranging from about 30% to about 80%. As discussed above, the preferred porous material is a microporous synthetic sheet commercially available from PPG Industries, Inc., under the trademark Teslin®. Due to the high porosity of backing layer 26, the hydrogel layer 42 on the first side 36 of support layer 34 creates an adhesive-like bond between itself and the second side 30 of backing layer 26. The use of a porous layer such as the above-described backing layer 26 obviates the need for a separate adhesive layer between hydrogel layer 42 and backing layer 26. Together, the backing layer 26, support layer 34 and hydrogel material 42 form a reinforced hydrogel patch 44.

The hydrogel patch 44 is preferably assembled in a sheet form and subsequently cut into various pieces of desired size and shape. The size and shape of the thin-film layer 14 are selected so as to accommodate the hydrogel patch 44. The hydrogel patch 44 is then laminated to the center portion 16 of thin-film layer 14 such that the first side 28 of backing layer 26 adheres to the second side 22 of thin-film layer 14 by means of adhesive layer 24.

A release liner 46, preferably silicone-coated, is provided. An optional removable tab 48 having first and second sides is also provided. The first side of tab 48 is laminated to one edge 50 of the perimeter portion 18 on the second side 22 of thin-film layer 14, such that the adhesive layer 24 is positioned between tab 48 and thin-film layer 14. A first side of release liner 46 is then laminated to the perimeter portion 18 on the second side 22 of thin-film layer 14 by means of adhesive layer 24. When the wound dressing product 10 is fully assembled, the release liner 46 overlies the hydrogel material 42 and hydrogel patch 44. In fact, the release liner 46, thin-film layer 14 and adhesive layer 24 form an adhesive seal around hydrogel material 42, thus preserving the sterility of the wound dressing product 10.

The preferred hydrogel material 42 is formed from an aqueous mixture including from about 0% to about 90% by weight polyhydric alcohol; from about 6% to about 60% by weight aliphatic diisocyanate-terminated prepolymer; from about 4% to about 40% by weight polyethylene oxide-based polyamine; up to about 2% by weight sodium chloride; and the balance water. A more preferred hydrogel composition for forming hydrogel layer 42 comprises from about 15% to about 30% by weight of a polyhydric alcohol selected from a group consisting of polypropylene glycol, polyethylene glycol and glycerine, from about 8% to about 14% by weight isophoronediisocyanate-terminated prepolymer, from about 5% to about 10% by weight polyethylene oxide-based diamine, up to about 1% by weight of a salt, and the remaining percentage water. Most preferably, the hydrogel material 42 includes 17% polypropylene glycol, 12% isophoronediisocyanate-terminated prepolymer, 9% polyethylene oxide-based diamine, 1% salt, and 61% water. The hydrogel material 42 provides a biocompatible, nonirritating, fluid-absorbing, bacterial-protective, cushioning, skin-like media over the wound site.

In one method of manufacture, a flat tab 48, constructed of a double-coated paper, polystyrene, polyester, or any other suitable material, is provided. In a second embodiment, a V-shaped member 56, preferably silicone-coated, is provided in place of flat tab 48. The V-shaped member 56 has a first flap 58 and a second flap 60. The first flap 58 is secured to the second side 22 of the thin-film layer 14 by adhesive layer 24, while the second flap 60 is positioned between the first flap 58 and release liner 46. The open end of the "V" is positioned along one edge 50 of thin-film layer 14 and the opposing edge 52 of release liner 46. Both the tab 48 and the V-shaped member 56 are removable by peeling after the wound dressing 12 is applied to the patient's skin.

Alternatively, flat tab 48 and V-shaped member 56 may be eliminated altogether. In their place, thin-film layer 14 is provided with a nonadhesive portion 64, as shown in FIG. 2, in order to facilitate removal of the thin-film layer 14 from release liner 46 prior to application of the wound dressing 12 to the wound.

The wound dressing product 10 of the present invention is particularly advantageous for use on exuding wounds. In particular, a special feature of the hydrogel material 42 is that it retains its gel-like integrity even upon removal of the wound dressing 12 from a wound site. The hydrogel material 42 does not leave debris in the wound when the wound dressing 12 is removed, nor does it adhere to the wound site. The benefit of this feature is that the hydrogel material 42 exhibits a capability of nontraumatically releasing from the wound when the wound dressing 12 is removed, so as to not destroy new cell tissue forming at the wound site. Thus, healing is not inhibited by removal of the dressing 12. A further benefit of the present invention is that the porous backing layer 26 allows for attachment of the hydrogel material 42 directly to the backing layer 26 without the use of a separate adhesive layer. The use of the porous material, therefore, results in a wound dressing product that is simpler and less expensive to manufacture.

Having described the invention in detail and by reference to preferred embodiments thereof, it will be apparent that modifications and variations are possible without departing from the scope of the invention which is defined in the appended claims.

What is claimed is:

1. A method of manufacturing a wound dressing product for a wound, comprising the steps of:

providing a thin-film layer having a first side and a second side and further having a perimeter portion and a center portion;

coating said second side of said thin-film layer with an adhesive layer;

providing a porous backing layer having first and second opposing sides;

providing a support layer having a first side and a second side, said support layer comprising a permeable fabric having a plurality of interstices therewith;

applying a hydrogel material directly to said second side of said support layer, wherein said hydrogel material penetrates said interstices to said first side of said support layer such that said hydrogel material resides on both said first side and said second side of said support layer;

laminating said first side of said support layer to said second side of said backing layer, wherein said hydrogel material located on said first side of said support layer adheres to said second side of said backing layer, such that said backing layer, said support layer and said hydrogel material collectively form a reinforced hydrogel patch;

laminating said hydrogel patch to said center portion of said thin-film layer, wherein said first side of said backing layer adheres to said second side of said thin-film layer by means of said adhesive layer;

providing a release liner having a first side and a second side;

laminating said first side of said release liner to said perimeter portion of said second side of said thin-film layer, whereby said adhesive layer is positioned between said thin-film layer and said release liner.

2. A method of manufacturing a wound dressing product as claimed in claim 1, wherein the step of providing a porous backing layer comprises the step of providing a backing layer formed of a porous material having sufficient porosity such that said second side of said backing layer is securable to said hydrogel material.

3. A method of manufacturing a wound dressing product as claimed in claim 1, wherein the step of providing a porous backing layer comprises the step of providing a backing layer formed of a filled polyolefin foam.

4. A method of manufacturing a wound dressing product as claimed in claim 1, wherein said reinforced hydrogel patch is formed in a sheet and cut to a desired size, and the size of said thin-film layer is selected so as to accommodate said hydrogel patch.

5. A method of manufacturing a wound dressing product as claimed in claim 1, further comprising the steps of:

providing at least one removable tab having a first side and a second side, so as to provide a grippable surface to facilitate the removal of said release liner from said thin-film layer and to facilitate the handling of said wound dressing during application of said dressing to a wound; and laminating said first side of said tab to one edge of said perimeter portion of said second side of said thin-film layer, whereby said adhesive layer is positioned between said tab and said thin-film layer, and said tab is positioned between said adhesive layer and said release liner.

6. A method of manufacturing a wound dressing product as recited in claim 1, wherein said hydrogel material comprises:

(a) from about 0% to about 90% by weight polyhydric alcohol;

(b) from about 6% to about 60% by weight aliphatic diisocyanate-terminated prepolymer;

(c) from about 4% to about 40% by weight polyethylene oxide-based polyamine;

(d) up to about 2% by weight sodium chloride; and (e) the balance water.

7. A method of manufacturing a wound dressing product as recited in claim 1, wherein said hydrogel material comprises:

(a) from about 15% to about 30% by weight polyhydric alcohol;

(b) from about 8% to about 14% by weight isophorone diisocyanate-terminated prepolymer;

(c) from about 5% to about 10% by weight polyethylene oxide-based diamine;

(d) up to about 1% by weight sodium chloride; and (e) the balance water.

8. A method of manufacturing a wound dressing product as recited in claim 1, wherein said hydrogel material comprises:

(a) about 17% by weight polypropylene glycol;

(b) about 12% by weight isophorone diisocyanate-terminated prepolymer;

(c) about 9% by weight polyethylene oxide-based diamine;

(d) about 1% by weight sodium chloride; and (e) about 61% by weight water.

\* \* \* \* \*